(12) United States Patent
Zieger et al.

(10) Patent No.: US 12,357,169 B2
(45) Date of Patent: Jul. 15, 2025

(54) REFRACTIVE INDEX DETERMINATION BY MULTI-DIRECTIONAL OPHTHALMIC IMAGE PROCESSING

(71) Applicant: Alcon Inc., Fribourg (CH)

(72) Inventors: Peter Zieger, Teltow (DE); Tillmann Wieland, Berlin (DE); Martin Gründig, Rangsdorf (DE)

(73) Assignee: ALCON INC., Fribourg (CH)

( * ) Notice: Subject to any disclaimer, the term of this patent is extended or adjusted under 35 U.S.C. 154(b) by 412 days.

(21) Appl. No.: 17/945,884

(22) Filed: Sep. 15, 2022

(65) Prior Publication Data
US 2023/0119409 A1 Apr. 20, 2023

Related U.S. Application Data

(60) Provisional application No. 63/257,268, filed on Oct. 19, 2021.

(51) Int. Cl.
| | |
|---|---|
| *A61B 3/10* | (2006.01) |
| *A61B 3/00* | (2006.01) |
| *A61B 3/103* | (2006.01) |
| *A61B 3/14* | (2006.01) |
| *A61B 3/15* | (2006.01) |

(52) U.S. Cl.
CPC ............ *A61B 3/0025* (2013.01); *A61B 3/103* (2013.01); *A61B 3/152* (2013.01)

(58) Field of Classification Search
CPC ........ A61B 3/0025; A61B 3/103; A61B 3/152
USPC ........................................ 351/206, 209, 211
See application file for complete search history.

(56) References Cited

U.S. PATENT DOCUMENTS

2021/0038071 A1    2/2021  Tatara et al.

FOREIGN PATENT DOCUMENTS

| JP | 2018149449 A | 9/2018 |
|---|---|---|
| JP | 2020151094 A | 9/2020 |

*Primary Examiner* — Mahidere S Sahle (57) ABSTRACT

The present disclosure provides a non-invasive technique to determine a true set of refractive indices of a patient's eye in order to generate an accurate model of the patient's eye. Certain aspects provide a system for generating a three-dimensional reconstruction model of a patient's eye. The system includes an imaging device configured to generate first and second measurements of a patient's eye at first and second angles relative to a line of sight of the patient's eye. The system includes an image processor configured to generate a first and second plurality of models of the patient's eye based on applying a plurality of sets of refractive indices to the first and second measurements; identify a first model from the first plurality of models that is congruent with a second model from the second plurality of models; and determine a set of refractive indices associated with the first and second models.

15 Claims, 7 Drawing Sheets

REFRACTIVE INDEX DETERMINATION BY MULTI-DIRECTIONAL OPHTHALMIC IMAGE PROCESSING

BACKGROUND

Ophthalmic imaging techniques, such as optical coherence tomography (OCT), confocal scanning laser ophthalmoscopy, and scanning laser polarimetry, try to model the physical shapes of the optical components of the eye. The optical components of the eye include the cornea, aqueous humor, lens, vitreous humor, and retina. To reconstruct a geometric model of the optical components of the eye, the refractive indices of the optical components inside the eye are needed.

Anatomically, the eye is divided into two distinct regions—the anterior segment and the posterior segment. The anterior segment includes the lens and extends from the outermost layer of the cornea (the corneal endothelium), also referred to as the anterior surface of the cornea, to the lens. The aqueous humor fills the space between the lens and the cornea and helps maintain intraocular pressure. The posterior segment includes the portion of the eye behind the lens. The posterior segment includes the vitreous humor-a clear, colorless, gel-like substance that makes up approximately two-thirds of the eye's volume. The vitreous humor fills the space between the lens and the retina.

The human eye has a gradient of refractive index, which typically increases from the edge to the center of the eye. The cornea, aqueous humor, lens, and vitreous humor each has a different index of refraction. Generally, when using ophthalmic imaging techniques, the refractive indices are not known. Instead, averaged, patient-independent values for the refractive indices of the optical components are assumed. For a true reconstruction of the optical components, however, the actual patient-specific set of refractive indices are needed. Currently, there exists a lack of direct, non-invasive measurement techniques to determine all refractive indices of the optical components of the eye. Current methods are invasive or destructive.

SUMMARY

Aspects of the present disclosure provide a system for generating a three-dimensional reconstruction model of a patient's eye. The system generally includes an imaging device. The imaging device is configured to generate first measurements of a patient's eye at a first angle relative to a line of sight of the patient's eye. The imaging device is configured to generate second measurements of the patient's eye at a second angle relative to the line of sight of the patient's eye. The system generally includes an image processor. The image processor is generally configured to generate a first plurality of models of the patient's eye based on applying a plurality of sets of refractive indices to the first measurements. The image processor is generally configured to generate a second plurality of models of the patient's eye based on applying the plurality of sets of refractive indices to the second measurements. The image processor is generally configured to identify a first model from the first plurality of models that is congruent with a second model from the second plurality of models. The image processor is generally configured to determine a set of refractive indices from the plurality of sets of refractive indices associated with the first model and the second model.

Aspects of the present disclosure also provide a method for generating a three-dimensional reconstruction model of a patient's eye. The method generally includes generating first measurements of a patient's eye at a first angle relative to a line of sight of the patient's eye. The method generally includes generating second measurements of the patient's eye at a second angle relative to the line of sight of the patient's eye. The method generally includes generating a first plurality of models of the patient's eye based on applying a plurality of sets of refractive indices to the first measurements. The method generally includes generating a second plurality of models of the patient's eye based on applying the plurality of sets of refractive indices to the second measurements. The method generally includes identifying a first model from the first plurality of models that is congruent with a second model from the second plurality of models. The method generally includes determining a set of refractive indices from the plurality of sets of refractive indices associated with the first model and the second model.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is noted, however, that the appended drawings illustrate only some aspects of this disclosure and the disclosure may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure provides a non-invasive technique to determine a true set of refractive indices of a patient's eye in order to generate an accurate model of the patient's eye. The model of the patient's eye can be used for making predictions.

For example, in the field of cataract surgery, the model can be used to form an accurate prediction of the patient's vision in order to select the correct lens to place inside the patient's eye. Cataract surgery involves removing a cataractous lens of a patient's eye and replacing the lens with an artificial intraocular lens (IOL). Planning for cataract surgery typically involves selecting an IOL with an IOL power that is able to achieve a desired refractive outcome or target post-surgery. The determination of an IOL power necessary to achieve a particular post-operative refraction outcome is dependent on measurements of the anatomical parameters of the patient's eye, such as one or more of the axial length of the eye, corneal curvature, anterior chamber depth, white-to-white diameter of the cornea, lens thickness, an effective lens position, etc. For example, using a patient's measurements, certain existing systems estimate a post-operative manifest refraction in spherical equivalent (MRSE), e.g., for each of a given set of IOL powers available on the market. Using the post-operative MRSEs, the surgeon may then select the IOL power that results in an estimated post-operative MRSE that is closest to the refractive target (i.e., has the lowest estimated post-operative refractive error). For true values of the MRSE, however, accurate patient-specific values are needed.

The model of the patient's eye with the true refractive indices can also be used in determining the actual conditions within the patient's eye for other diagnostic and treatment purposes (e.g., such as with respect to retinal disease).

The true set of refractive indices may be determined based on measurements of the patient's eye. The measurements of the patient's eye can be made with an ophthalmic imaging system, which may use optical coherence tomography (OCT), aberrometry, or reflection-based, or a combination of ophthalmic imaging techniques. The measurements are performed at multiple incident beam directions, such as by varying the angle of a light ray incident to the patient's eye (e.g., by changing the rotation and/or position of the imaging device) or by varying the patient's line of sight while taking measurements in relation to a light ray incident to the patient's eye (e.g., by directing the patient to rotate or change the position of their eye).

Based on the incident beam direction and the measurements taken at the different incident beam directions, detailed geometric conditions within the eye can be determined. For each different angle of incidence, three-dimensional (3D) reconstructions of the optical components can be generated using different sets of refractive indices for the individual optical components. When using the true set of refractive indices, the 3D reconstructions generated for each incident beam direction will be congruent.

Accordingly, by comparing the 3D reconstructions generated from the measurements at the different incident beam directions, the set of true refractive indices can be determined by finding the set of refractive indices that generates a common 3D reconstruction (e.g., within an acceptable error amount) of the patient's eye across multiple incident beam directions.

Figure 1:
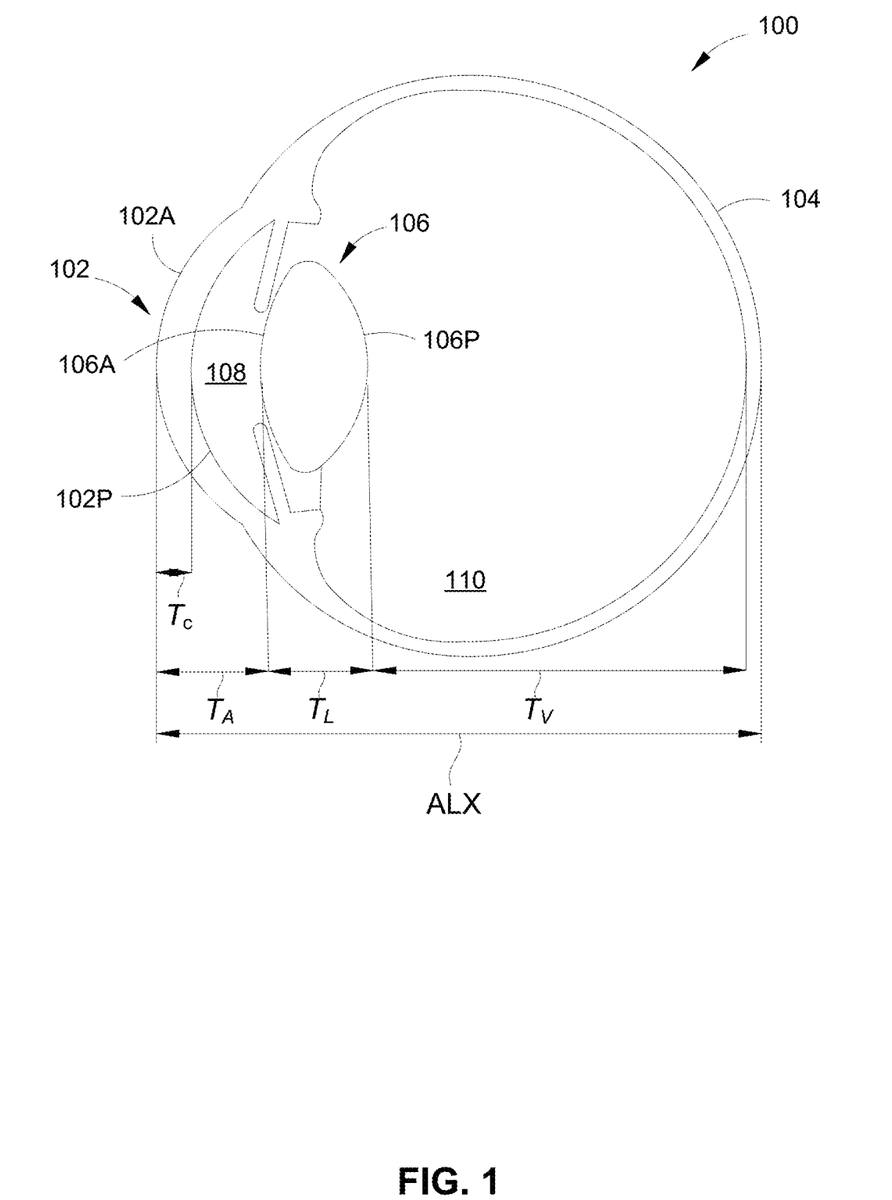
FIG. 1 is a schematic view of a model patient's eye, according to certain aspects.

FIG. 1 is a schematic view of a model patient's eye 100, according to certain aspects. As shown, the model patient's eye 100 includes a cornea 102, a retina 104, a lens 106, an aqueous humor 108, and a vitreous humor 110. Model eye 100 has an overall axial length, ALX (i.e., the distance between anterior surface 102A of cornea 102 and retina 104). Cornea 102 has a refractive index, $n_{cornea}$. Cornea 102 has an anterior surface 102A with a radius of curvature, $R_A$, and a posterior surface 102P with a radius of curvature, $R_P$. Cornea 102 has a thickness, $T_C$ (i.e., distance between posterior surface 102P and anterior surface 102A). The thickness of cornea 102 is not constant, but is a composition of local thicknesses across cornea 102. Aqueous humor 108 fills the space between cornea 102 and lens 106. Aqueous humor 108 has a refractive index, $n_{aqueous}$. Aqueous humor 108 has a depth, $T_A$ (i.e., the distance between posterior surface 102P of cornea 202 to the anterior surface 106A lens 106). Lens 106 has a refractive index, $n_{lens}$ and thickness, $T_L$ (i.e., the distance between anterior surface 106A and posterior surface 106P of lens 106). Vitreous humor 110 has a depth, $T_V$ (i.e., the distance between lens 106 and retina 104) and a refractive index, $n_{vitreous}$.

Figure 2:
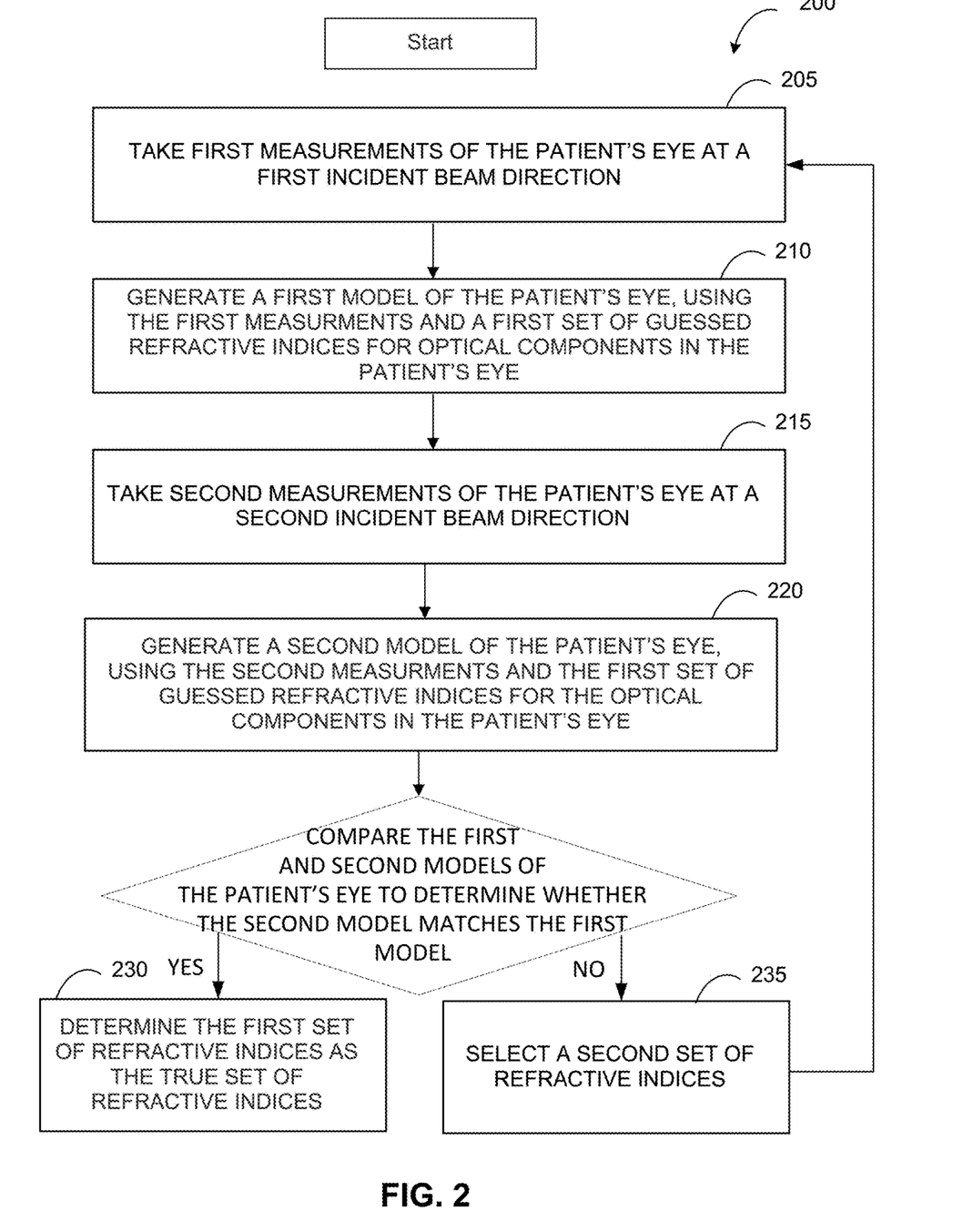
FIG. 2 is a decision tree diagram illustrating example operations for determining a true set of refractive indices for the patient's eye of FIG. 1, according to certain aspects.

FIG. 2 is a decision tree diagram illustrating example operations 200 for determining a true set of refractive indices, $n_{cornea}$, $n_{aqueous}$, $n_{lens}$, and $n_{vitreous}$ for the optical components of the model patient's eye 100 of FIG. 1, according to certain aspects. Operations 200 may be performed by an ophthalmic imaging system. Operations 200 in FIG. 2 may be understood with respect to, and is described in connection with, the description of FIGS. 3-6.

Operations 200 may begin, at 205, by taking first measurements of the patient's eye (e.g., the model patient's eye 100) at a first incident beam direction.

The measurements can be taken by various devices or techniques. Reflection-based ophthalmic techniques involve measuring light reflected back from optical components within the eye. OCT is an imaging technique based on low-coherence interferometry that uses low-coherence light to capture 2D and 3D images from within optical scattering media (e.g., biological tissue in the eye). With respect to OCT, the use of relatively long wavelength light allows the light to penetrate into the scattering medium.

Ophthalmic aberrometry can be used to detect aberrations in the eye using a wavefront aberrometer that analyzes differences between distorted wavelengths of light reflected from a patient's eye with respect to wavelengths of light reflected from a normal eye. As light (e.g., monochromatic light rays input to the patient's eye through the pupil) passes through the eye, the front of the light wave presents a flat shape, where irregularities in the wavefront shape of light rays reflected back represent distortions in the path the light travels.

Figure 3:
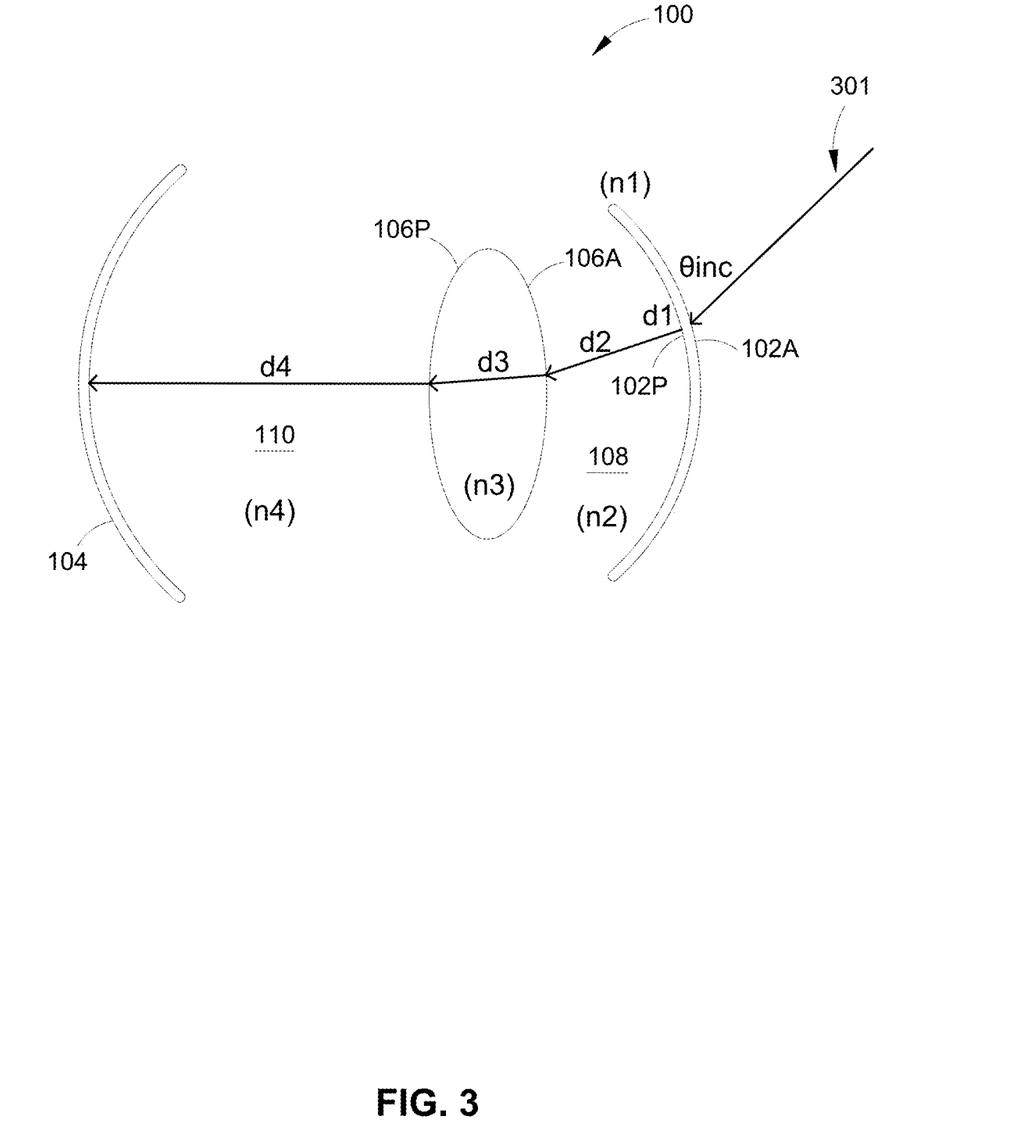
FIG. 3 is a schematic view of a light ray passing through the patient's eye of FIG. 1, according to certain aspects.

In certain embodiments, one or more of the ophthalmic imaging techniques or devices described above may use an optical signal (e.g., a laser). As shown in FIG. 3, a light ray 301 is propagated into the patient's eye 100. FIG. 3 is a schematic view of light ray 301 passing through the patient's eye 100 of FIG. 1 for generating ophthalmic imaging of the patient's eye 100, according to certain aspects. In some embodiments, an ophthalmic imaging device directly or indirectly measures a time delay for light ray 301 to travel into the patient's eye 100 and reflect back from various optical components within the patient's eye 100. The time delay can be measured using light tracing (also referred to as ray tracing) techniques, as known to one of ordinary skill in the art.

The path taken by light ray 301 (e.g., the local distances d1, d2, d3, d4 discussed below) is defined by the refraction due to the refractive indices of the components in the eye 100 at each transition between the optical components in the patient's eye 100. The angle at which light ray 301 enters anterior surface 102A of cornea 102 is referred to as the angle of incidence, $\theta_{inc}$. Based on the refractive index, $n_{cornea}$ (n1), of cornea 102, light ray 301 will be refracted and travel a local distance, d1, between anterior surface 102A and posterior surface 102P of cornea 102. After passing through cornea 102, light ray 201 will be refracted based on the refractive index, $n_{aqueous}$ (n2), of aqueous humor 108 and travels a local distance, d2, between posterior surface 102P of cornea 102 and anterior surface 106A of lens 106. At lens 106, light ray 301 will be refracted based on the refractive index, $n_{lens}$ (n3), of lens 106 and travels a local distance, d3, between anterior surface 106A and posterior surface 106P of lens 106. After passing through lens 106, light ray 301 will be refracted based on the refractive index, $n_{vitreous}$ (n4), of vitreous humor 110 and travels a local distance, d4, between posterior surface 106P of lens 106 and retina 104. In some embodiments, the first measurements, at 205, may be taken for multiple light rays (e.g., a 3D ray or bundle or rays) at the same angle of incidence, $\theta_{inc}$.

After taking measurements of the patient's eye, at 205, operations 200 may proceed to generating a first model of the patient's eye 100, using the first measurements and a first set of guessed refractive indices (e.g., $n_{start}$, for the optical components in the patient's eye 100. In some embodiments, ray tracing is used to trace light ray 301 through the patient's eye 100 by calculating the angle of refraction/reflection at each surface. Using the measured time delays for reflections of light ray 301 from the optical components in the patient's eye 100 to be received at the imaging device, the local distances travelled by light ray 301 in the patient's eye 100 can be computed using the formula:

$t=n*c*d$, which gives $d=t/(n*c)$, where t is the time delay measured between reflections of light ray 301 from two optical components, n is the index of refraction, c is the speed of light (i.e., a known constant of approximately $3*10^8$ m/s), and d is the local distance the light travelled between the two optical components.

For example, the ophthalmic imaging device can observe partial reflections of light ray 301 from each of the optical components of the patient's eye 100—i.e., from cornea 102, anterior surface 106A of lens 106, posterior surface 106P of lens 106, and retina 104. Counting from when the partial reflections are observed, time delays can be determined from when light ray 401 is transitioning from the air to anterior surface 102A of cornea 102, from posterior surface 102P of cornea 102 to aqueous humor 108, from aqueous humor 108 to lens 106, from lens 106 to vitreous humor 110, and from vitreous humor 110 to retina 104. These time delays can be used with selected "guessed" refractive indices to compute a local distance travelled by light ray 301. The initial guessed refractive indices may be patient-independent values, such as commonly-used or average refractive indices (e.g., from research, a textbook, etc.) or may be customized values (e.g., guessed based on additional information from previous procedures on the patient, similar patient demographics, etc.).

To get d1, the local distance light ray 301 travels through cornea 102, the time delay, $t_{cornea}$, may be computed based on a difference between a time, $t_1$, when a first partial reflection of light ray 301 from anterior surface 102A of cornea 102 is received at the imaging device and a time, $t_2$, when a second partial reflection of light ray 301 from posterior surface 102P of cornea 102 is received at the imaging device. An initial "guessed" value, n1, is selected for $n_{cornea}$. The local distance, d1, that light ray 301 travels between anterior surface 102A and posterior surface 102P may then be computed as $d1=[t_{cornea}/(c*n1)]$. Values for the local distances d2, d3, and d4 that light ray 301 travels between the other optical components may be computed similarly, using the measurements and initial guessed values for $n_{aqueous}$, $n_{lens}$, and $n_{vitreous}$. The refractive index of the lens may be a gradient. Accordingly, in some embodiments, the refractive index of the lens may be determined as multiple refractive indices or a distribution of refractive indices represented by a function.

A 3D model of the patient's eye 100 can be generated based on the computed values for the local distances d1, d2, d3, and d4, as well as angles of refraction/reflection at each of the optical components. The angles of refraction/reflection can be determined using tracing. The distances can be computed from the measurements of light ray 301 taken at the first angle of incidence, $\theta_1$, (e.g., defined by a rotation $R_{start}$ position $X_{start}$ of the patient's eye 301 with respect to the imaging device) and the set of initial refractive indices, $n_{start}$. As mentioned above, in some embodiments, measurements can be taken for multiple light rays (e.g., using a 3D ray or a bundle of rays) with the same angle of incidence.

The operations 205 and 210 can then be repeated, but using a light ray (or multiple light rays) propagated to the patient's eye at a second angle of incidence, $\theta_2$. At 215, the ophthalmic imaging device takes second measurements of the patient's eye at a second incident beam direction. At 220, a second model of the patient's eye is generated using the second measurements and the first set of guessed refractive indices for the optical components in the patient's eye.

To obtain the measurements of the patient's eye from different alignments, the measurement device can be moved relative to the patient's eye or the patient's eye can be moved relative to the device (e.g., by asking the patient to move their eye to look at static or dynamic targets located at different alignments relative to the patient's position or physically moving the patient relative to the device to create the different alignments). The different incident beam directions are selected from within a range of angles having a maximum angle. The maximum angle may be an angle that results in a minimum amount of the incident light entering the patient's eye 100 through the pupil and passing through the respective optical components within the patient's eye 100. An angle of 0 degrees may result in a maximum amount of the incident light entering the patient's eye 100 through the pupil. In some embodiments, a difference between the first and second incident beam directions may be less than a specified threshold. In some embodiments, incident beam directions may be used that provide a threshold coverage of retina 104. When the incident beam direction changes, an indicator may be provided to an operator of the system that indicates a change of the incident beam direction.

Figure 4:
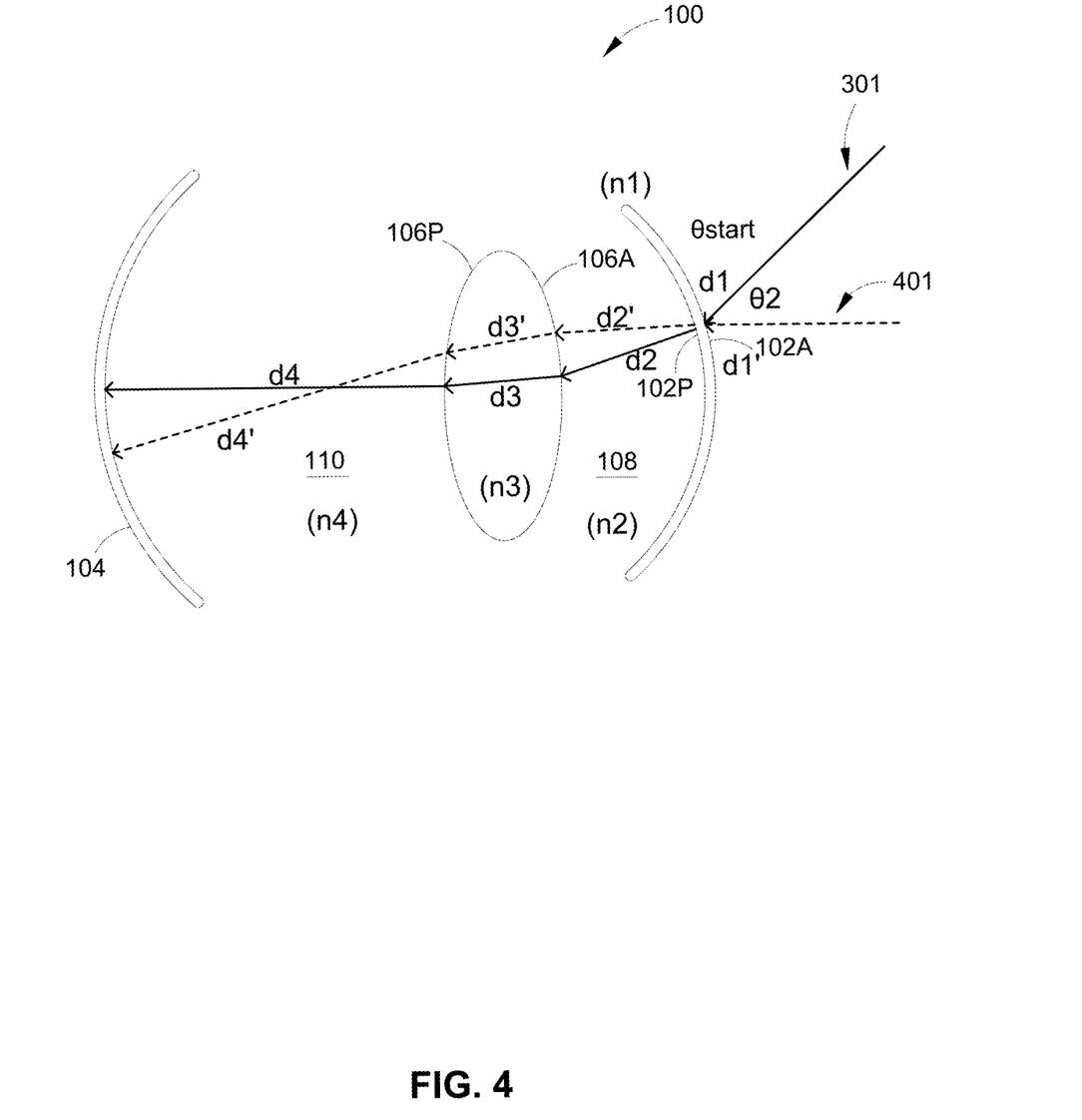
FIG. 4 is a schematic view of multiple light rays passing through the patient's eye of FIG. 1 with different incident beam directions, according to certain aspects.

FIG. 4 is a schematic view of multiple light rays, 301 and 401, passing through the patient's eye 100 of FIG. 1 at different incident beam directions for performing ophthalmic imaging of the patient's eye 100, according to certain aspects. As shown in FIG. 4, measurements of another light ray 401 (e.g., a 3D ray or bundle of rays) input at a second angle of incidence, $\theta_2$, can be taken to obtain the local distances d1', d2', d3', and d4' travelled by light ray 401 through the optical components of the patient's eye 100 using the same initial values for the set of refractive indices.

Another 3D model of the patient's eye 100 can be generated based on the computed values for the distances d1', d2', d3', and d4', as well as the angles of refraction/reflection at each of the optical components which can be obtained from the ray tracing for measurements of light ray 401 taken at the first angle of incidence (e.g., defined by a rotation $R_{second}$ and position $X_{second}$ of the patient's eye 401 with respect to the imaging device) and using the same set of initial refractive indices, $n_{start}$. As mentioned above, in some embodiments, measurements can be taken for multiple light rays (e.g., using a 3D ray or a bundle of rays) with the same angle of incidence.

The initial guessed set of refractive indices, $n_{start}$, can be verified by comparing the 3D models. If $n_{start}$ corresponds to the true set of refractive indices, then the models generated from measurements at different incident beam directions should match each other. Accordingly, at 225, the first model of the patient's eye and the second model of the patient's eye are compared, as described further below with respect to FIGS. 5-6, to determine whether they match (e.g., match within a specified error tolerance). In this example, 3D models generated from measurements at two different incident beam directions are compared, however, 3D models from more than two different incident beam directions may be generated and compared to verify the set of refractive indices.

If the models do not match, the "guessed" refractive indices used to generate the models are determined not to be the true set of refractive indices. At 235, a different, second, set of refractive indices, $n_{second}$, is selected and the operations 205-225 are repeated using the second set of refractive indices. Operations 200 can be repeated until the true set of refractive indices are found and the models generated based on measurements with different incident beam directions are a match.

Figure 5:
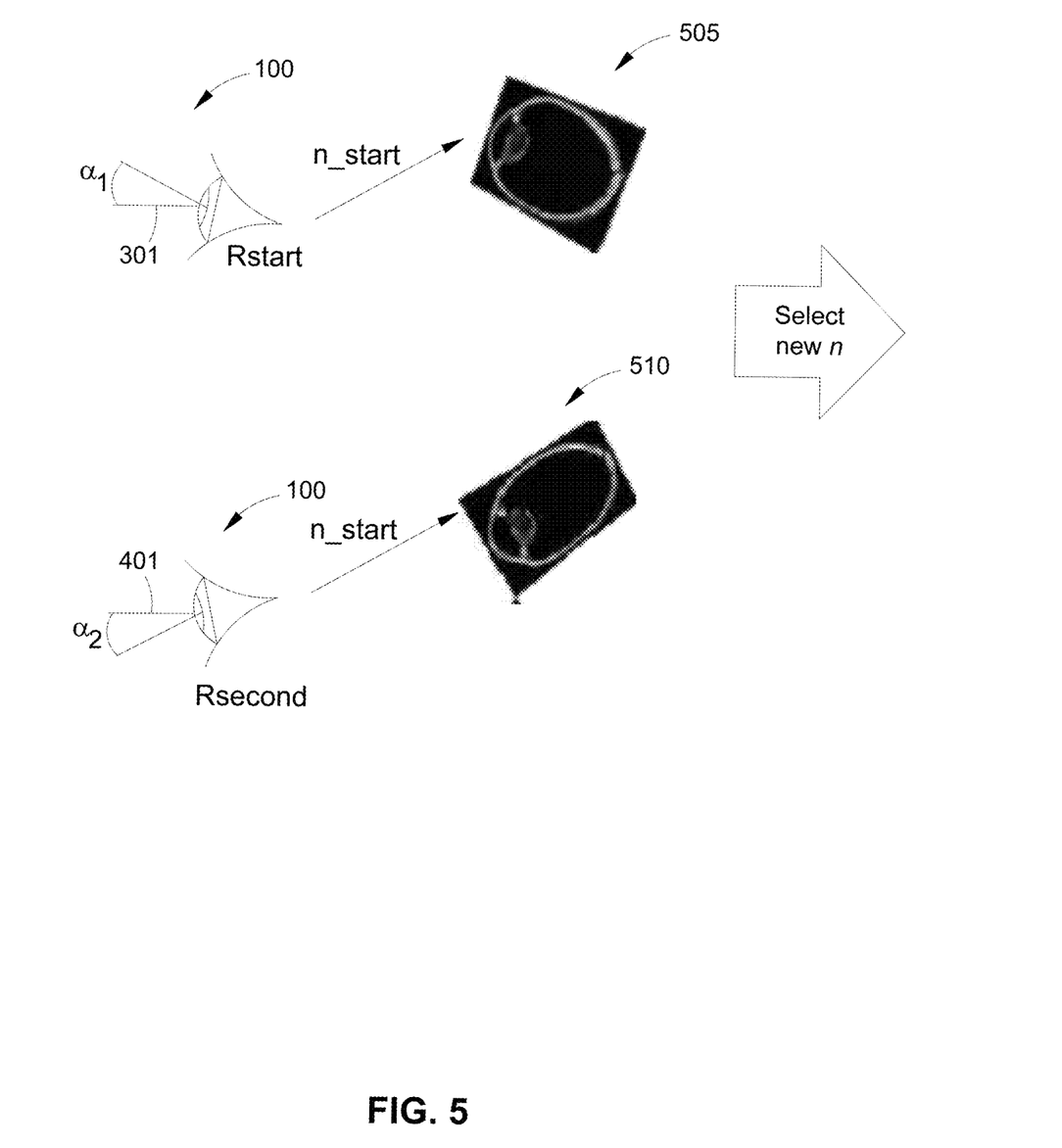
FIG. 5 is a schematic view illustrating an example of mismatching models of the patient's eye of FIG. 1, according to certain aspects.

FIG. 5 is a schematic view illustrating an example of mismatching models of the patient's eye 100 of FIG. 1, according to certain aspects. As shown in FIG. 5, based on the measurements of light ray 301 taken at the first angle of incidence, $\theta_1$, and using the initial set of refractive indices, $n_{start}$, a first 3D model 505 of the patient's eye 100 is generated. Further, based on the measurements of light ray 401 taken at the second angle of incidence, $\theta_2$, and using the same initial set of refractive indices, $n_{start}$, a second 3D model 510 of the patient's eye 100 is generated. The models 505 and 510 are then compared to determine whether they are match. As shown in FIG. 5, the models 505 and 510 do not match (e.g., model 510 has a narrower more elliptical shape than model 505). Accordingly, a new set of refractive indices are selected.

Figure 6:
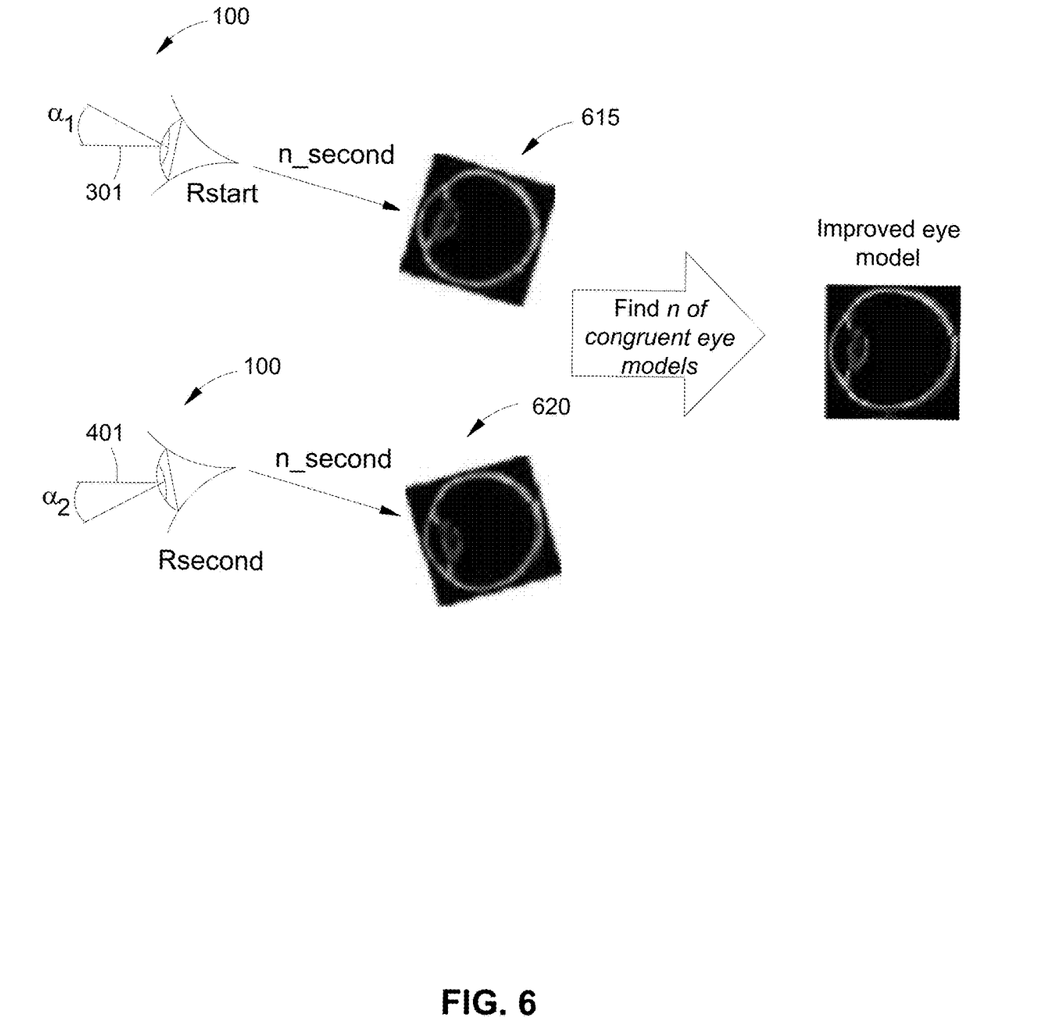
FIG. 6 is a schematic view illustrating an example of matching models of the patient's eye of FIG. 1, according to certain aspects.

If the models match, then the set of refractive indices, $n_{start}$, are determined to be the true set of refractive indices, $n_{true}$, at 230, and the process of determining the set of refractive indices ends. FIG. 6 illustrates an example of matching models, according to certain aspects. As shown in FIG. 6, based on the measurements of light ray 401 taken at a third angle of incidence, $\theta_3$ (e.g., which may be the same or a different angle than the angles used for the previous measurements), and using the second set of refractive indices, $n_{second}$, a third 3D model 615 of the patient's eye 100 is generated. Further, based on the measurements of light ray 401 taken at a fourth angle of incidence, $\theta_4$ (which is different than the third angle), and using the same second set of refractive indices, $n_{second}$, a fourth 3D model 620 of the patient's eye 100 is generated. The models 615 and 620 are then compared to determine whether they match. As shown in FIG. 6, the models 615 and 620 are a match (e.g., model 515 has the same shape as the model 620). Accordingly, the second set of refractive indices are determined to be the true set of refractive indices, $n_{true}$.

In some embodiments, comparing the models first involves alignment of the models. As shown in FIG. 5 and FIG. 6, the models are not aligned. For example, model 505 is generated based on the patient's eye 100 having the first rotation, $R_{start}$, and the first position, $X_{start}$, and the model 510 is generated based on the patient's eye 100 having the second rotation, $R_{second}$, and the second position, $X_{second}$. The models 505 and 510 may be aligned (not shown) to each other by adjusting to a rotation of the first and/or second model to a rotation, $R_{aligned}$, and/or a position, $X_{aligned}$. Similarly, the models 615 and 620 may be aligned. In some embodiments, the models 505 and 510 may be aligned with respect to the plane of the anterior surface 102A of the cornea 102. The alignment may be performed using an optimization function. The alignment may be performed by a transformation (e.g., in location, X, and/or rotation, R) applied to the models from a common point (e.g., anterior surface 102A or another point in the patient's eye 100) relative to a known coordinate system.

In an illustrative example, a patient is seated such that the 3D position of the patient's eye does not move substantially laterally or vertically. The measurement device is positioned directly horizontal and aligned with a center of the patient's right eye. The patient is told to look at a first target and a second target at different locations. The first target is positioned vertically above the second target such that there is no horizontal displacement or movement required to look at the different targets. The first target is positioned 30-degrees above a horizontal axis and the second target is positioned 15-degrees below the horizontal axis, where the horizontal axis passes through the center of the patient's eye (anterior cornea) when looking at the measurement device. Measurements A are captured when the patient is looking at the first target and measurements B are captured when the patient is looking at the second target without moving the measurement device. In the above example, the rotation matrix for measurement A may define the 30-degree rotation to look at the first target and the rotation matrix for measurement B may define the −15 degree rotation to look at the second target. Similarly, a translation vector can be applied if the location of the eye (e.g., the patient's head) changed between the measurements A and B, such that the 3D models are transformed into the same coordinate system.

Once aligned, the 3D models are compared to determine an error between them. In some embodiments, the 3D models can be compared visually (e.g., pixel by pixel). In some embodiments, machine learning can be used to compare the 3D models. In some embodiments, the 3D models can be compared mathematically, using an error metric. In some embodiments, the 3D models are compared using least squares or root mean square (RMS) error (RMSE) between the models. RMSE is the standard deviation of residuals (i.e., a measure of how data points are from a regression line). RMSE measures how spread apart residuals are. Residuals are the difference between actual values, $\hat{y}_i$, and predicted values, $y_i$. Squaring the residuals, averaging the squared, and taking the square root gives the RMSE:

$$RMSE = \frac{\sqrt{\sum_{i=1}^{n}(\hat{y}_i - y_i)^2}}{n}$$

For the 3D models of the patient's eye, the RMSE may be computed as:

$$error = \sqrt{\frac{\sum_{i=1}^{n}(d^iA_c - d^iB_c)^2 + (d^iA_{ac} - d^iB_{ac})^2 +}{(d^iA_{le} - d^iB_{le})^2 + (d^iA_{vit} - d^iB_{vit})^2}},$$

where n is the number of rays per measurement (e.g., per angle or incident beam direct), $dA_c$ is the local distance travelled within the cornea (d1) for measurements A at a first incident beam direction, $dB_c$ is the local distance travelled within the cornea (d1') for measurements B at a second incident beam direction, $dA_{ac}$ is the local distance travelled within the aqueous humor (d2) for measurements A at the first incident beam direction, $dB_{ac}$ is the local distance travelled within the aqueous humor (d2') for measurements B at the second incident beam direction, $dA_{le}$ is the local distance travelled within the lens (d3) for measurements A at the first incident beam direction, $dB_{le}$ is the local distance travelled within the lens (d3') for measurements B at the second incident beam direction, $dA_{vit}$ is the local distance travelled within the vitreous humor (d4) for measurements A at the first incident beam direction, and $dB_{vit}$ is the local distance travelled within the aqueous (d4') for measurements B at the second incident beam direction.

The RMSE provides a value between 0 and 1. If the RMSE value is at or above a threshold value, the models are determined not to match. If the RMSE value is below the threshold, then the models are determined to match.

In some embodiments, to account for discrete sampling (e.g., with a finite step size), resampling (e.g., by regression analysis) may be done to match the patterns between measurements.

Referring back to the FIG. 5, the models 505 and 510 can be determined not to match when the RMSE computed for the models is above a specified threshold. In this case, a new set of refractive indices are selected. In some embodiments, a gradient descent approach is used to reselect the values for the refractive indices. The goal is to minimize the error between the models. Based on the RMSE, the refractive indices can be optimized, meaning that the refractive indices are replaced until the error from the RMSE equation is minimized or less than a threshold value.

In some embodiments, the set of refractive indices for the optical components are optimized sequentially (i.e., from cornea to aqueous humor to lens to vitreous humor).

Accordingly, when the models do not match, a new guessed refractive index for the cornea may be selected, but the same guessed refractive indices for the aqueous humor, lens, and vitreous humor may be used. Once an optimized refractive index for the cornea is identified, the process can be repeated to optimize the refractive index for the aqueous humor, then the lens, and then vitreous humor. This is because the refractive index for the cornea can impact subsequent calculations.

Figure 7:
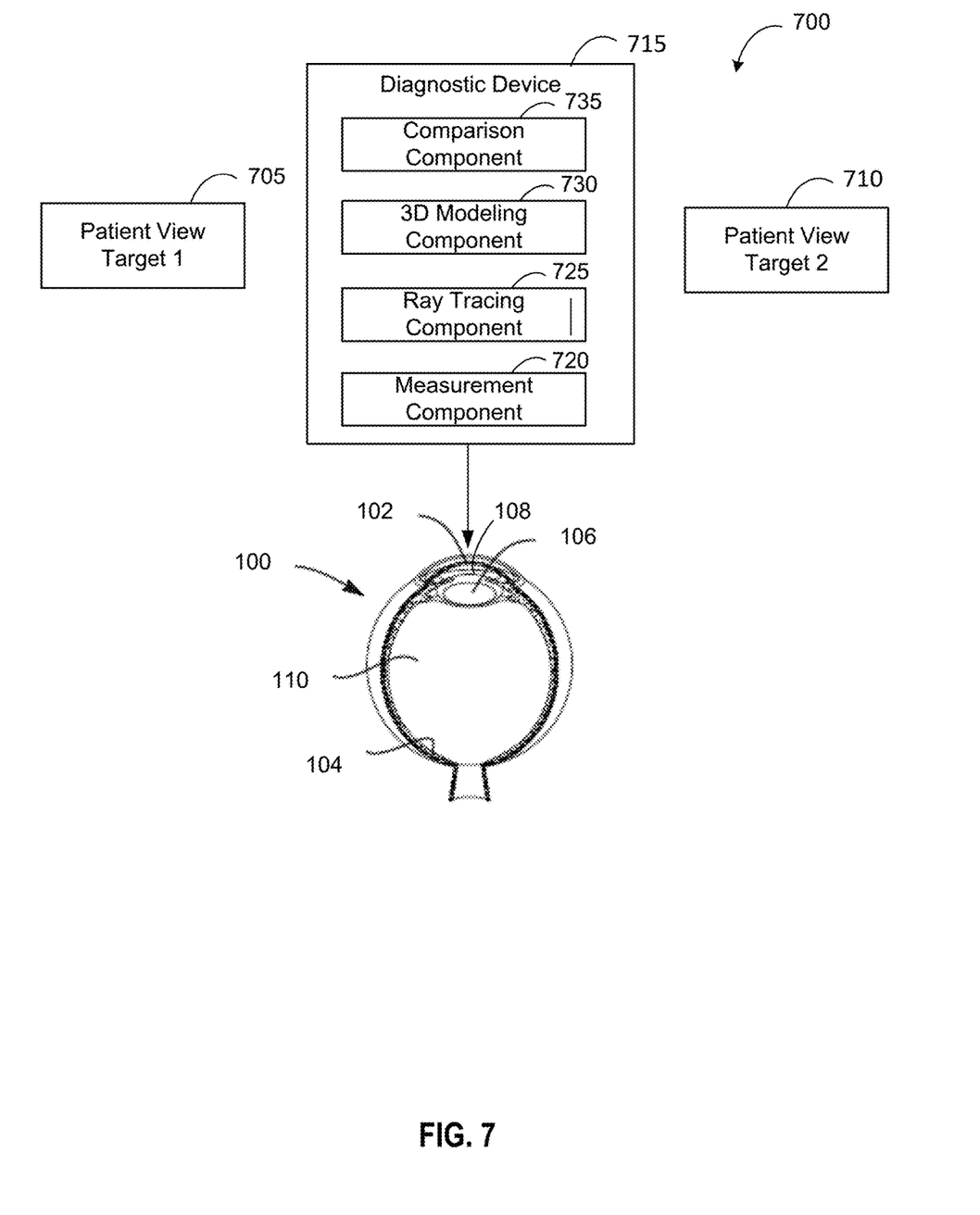
FIG. 7 is a diagram illustrating an example ophthalmic imaging system for determining a true set of refractive indices of optical components in a patient's eye, according to certain aspects.

FIG. 7 depicts an example system 700 for determining a true set of refractive indices of optical components in a patient's eye, according to certain aspects. As shown, system 700 includes, but is not limited to, a patient's eye 100, a diagnostic device 715, a first patient view target 705, and a second patient view target 710.

Diagnostic device 715 may be an OCT system, an aberrometer, or other ophthalmic diagnostic or imaging device. Device 715 may include at least a measurement component 720, ray tracing component 725, 3D modeling component 730, and comparison component 735.

Measurement component 720 is configured to take measurement of the patient's eye. For example, measurement component 720 may include an imaging device configured to measure time delays at which light rays are reflected back from optical components within the patient's eye 100. Measurement component 720 takes measurements from multiple different incident beam directions. Thus, in some embodiments, the patient may be directed to look at the first patient view target 705 while measurement component 720 takes a first set of measurements. While the patient is looking at the first patient view target 705, the patient's eye 100 will have a first rotation, $R_{start}$, defining a first angle with respect to an incident beam. The patient may be directed to look at the second patient view target 710 while measurement component 720 takes a second set of measurements. While the patient is looking at the second patient view target 710, the patient's eye 100 will have a second rotation, $R_{second}$, defining a second with respect to the incident beam. In some embodiments, the incident beam is a 3D beam or a bundle of beams. In some embodiments, the first and second patient view targets 705 and 710 is a single dynamic fixation target that changes locations.

Ray tracing component 725 may use the measurements from measurement component 720 to determine the paths followed by the incident beam within the patient's eye. Ray tracing component 725 may use a first set of guessed refractive indices, $n_{start}$, for the optical components of the eye. Ray tracing component 725 may determine angles of refraction at each transition between the optical components within the patient's eye 100 and the local distances d1, d2, d3, d4 travelled by the light rays within the patient's eye for the first angle of incidence. Ray tracing component 725 may also determine the angles of refraction and the local distances d1', d2', d3', and d4' travelled by the light rays within the patient's eye for the second angle of incidence.

Based on the ray tracing, 3D modelling component 730 can generate a first 3D model of the patient's eye 100 for the first angle of incidence and generate a second 3D model of the patient's eye 100 for the second angle of incidence. Ray tracing component 725 and modelling component 730 may comprise an image processor.

Comparison component 735 compares the 3D models to determine whether the models are congruent. Comparison component 735 may determine the RMSE between the models to find if the RMSE is within a specified threshold. If the RMSE for the models if not within the threshold, then diagnostic device 715 performs additional measurements, ray tracing, and 3D modeling to optimize the set of refractive indices according to the techniques discussed herein. Once comparison component 735 finds a set of congruent models, the true set of refractive indices are found and the model is considered the accurate model of the patient's eye. Comparison component 735 may be part of an image processor or a separate model processing component.

Although not shown, diagnostic device 715 may further include a light source configured to generate an optical signal (e.g., a bundle of light rays) and propagate the optical signal into the patient's eye. For OCT, the optical signal may use light rays in the near-infrared spectral range. Diagnostic device 715 may include one or more I/O device interfaces, which may allow for the connection of various I/O devices (e.g., keyboards, displays, mouse devices, pen input, etc.) for input from an operator.

Although not shown, diagnostic device 715 may also include one or more central processing units (CPUs), a memory, and a storage. The CPU may retrieve and execute programming instructions stored in the memory. Interconnects may transmits data, among the CPU, I/O device interface, a display, memory, and storage. A CPU have a single or multiple processing cores. Memory may be random access memory. Storage may a combination of fixed or removable storage devices, such as fixed disc drives, removable memory cards or optical storage, network attached storage (NAS), or a storage area-network (SAN).

The aspects described herein provides for determination of patient-specific refractive indices of the optical components in a patient's eye. Determination of the patient-specific set of refractive indices enables a more accurate model of the patient's eye to be generated. The accurate model of the patient's eye allows the actual conditions in the eye to be determined, which may be used for better assessing the patient's vision, more accurately computing refractive errors and selecting an IOL for the patient, and improved diagnosis of patient eye disease.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. A phrase referring to "at least one of" a list of items refers to any combination of those items, including single members and duplicate members. As an example, "at least one of: a, b, or c" is intended to cover, for example: a, b, c, a-b, a-c, b-c, a-b-c, aa, a-bb, a-b-cc, and etc.

While the foregoing is directed to embodiments of the present disclosure, other and further embodiments of the disclosure may be devised without departing from the basic scope thereof, and the scope thereof is determined by the claims that follow.

The invention claimed is:

1. A system for generating a three-dimensional reconstruction model of a patient's eye, the system comprising:
    an imaging device configured to:
        generate first measurements of a patient's eye at a first angle relative to a line of sight of the patient's eye; and
        generate second measurements of the patient's eye at a second angle relative to the line of sight of the patient's eye; and
    an image processor configured to:
        generate a first plurality of models of the patient's eye based on applying a plurality of sets of refractive indices to the first measurements;
        generate a second plurality of models of the patient's eye based on applying the plurality of sets of refractive indices to the second measurements;
        identify a first model from the first plurality of models that is congruent with a second model from the second plurality of models; and
        determine a set of refractive indices from the plurality of sets of refractive indices associated with the first model and the second model.

2. The system of claim 1, wherein the imaging device being configured to generate a first plurality of models and a second plurality of models of the patient's eye based on applying a plurality of sets of refractive indices to the first measurements and the second measurements, respectively comprises the imaging device being configured to:
    select a first set of refractive indices from the plurality of sets of refractive indices;
    generate a first model based on the first set of refractive indices;
    generate a second model based on the first set of refractive indices;
    identify differences of distances between features of the first model and the second model; and
    optimize the first set of refractive indices based on the differences such that the first model and the second model are congruent.

3. The system of claim 1, wherein:
    the imaging device is configured to generate the first measurements based on:
        projecting a first signal into the patient's eye at the first angle relative to the line of sight of the patient's eye; and
        capturing reflections of the first signal off of optical components of the patient's eye; and
    the imaging device is configured to generate the second measurements based on:
        projecting a second signal into the patient's eye at the second angle relative to the line of sight of the patient's eye; and
        capturing reflections of the second signal off of the optical components of the patient's eye.

4. The system of claim 3, wherein each set of refractive indices of the plurality of sets of refractive indices comprises a refractive index for at least one of the optical components of the patient's eye.

5. The system of claim 1, wherein a difference between the first angle relative to the line of sight of the patient's eye and the second angle relative to the line of sight of the patient's eye is obtained based on moving the imaging device relative to the patient's eye.

6. The system of claim 1, wherein a difference between the first angle relative to the line of sight of the patient's eye and the second angle relative to the line of sight of the patient's eye is obtained based on changing the line of sight of the patient's eye relative to the imaging device.

7. The system of claim 5, wherein the line of sight of the patient's eye relative to the imaging device is changed by varying a position of a dynamic fixation target between the first angle relative to the line of sight of the patient's eye and the second angle relative to the line of sight of the patient's eye.

8. The system of claim 1, further comprising a feedback system configured to:
    identify a change between the first angle and the second angle while maintaining a threshold coverage of a retina of the patient's eye; and
    provide an indicator of the change between the first angle and the second angle to an operator of the imaging device.

9. The system of claim 1, wherein the image processor being configured to determine the set of refractive indices associated with the first model and the second model comprises the image processor being configured to:
    identify an amount of time that a first signal spent traveling through each of respective optical components of the patient's eye;
    identify an amount of time that a second signal spent traveling through each of the respective optical components of the patient's eye; and
    calculate the set of refractive indices for the respective optical components of the patient's eye based on the amount of time from the first signal and the amount of time from the second signal.

10. The system of claim 8, wherein the image processor being configured to calculate the set of refractive indices comprises accounting for movement of the patient's eye within six degrees of freedom.

11. A method for generating a three-dimensional reconstruction model of a patient's eye, the method comprising:

generating first measurements of a patient's eye at a first angle relative to a line of sight of the patient's eye;

generating second measurements of the patient's eye at a second angle relative to the line of sight of the patient's eye;

generating a first plurality of models of the patient's eye based on applying a plurality of sets of refractive indices to the first measurements;

generating a second plurality of models of the patient's eye based on applying the plurality of sets of refractive indices to the second measurements;

identifying a first model from the first plurality of models that is congruent with a second model from the second plurality of models; and determining a set of refractive indices from the plurality of sets of refractive indices associated with the first model and the second model.

12. The method of claim 11, wherein generating the first plurality of models and the second plurality of models of the patient's eye based on applying a plurality of sets of refractive indices to the first measurements and the second measurements, respectively, comprises:

selecting a first set of refractive indices from the plurality of sets of refractive indices;

generating a first model based on the first set of refractive indices;

generating a second model based on the first set of refractive indices;

identifying differences of distances between features of the first model and the second model; and optimizing the first set of refractive indices based on the differences such that the first model and the second model are congruent.

13. The method of claim 11, wherein:

generating the first measurements comprises:
projecting a first signal into the patient's eye at the first angle relative to the line of sight of the patient's eye; and
capturing reflections of the first signal off of optical components of the patient's eye; and generating the second measurements comprises:
projecting a second signal into the patient's eye at the second angle relative to the line of sight of the patient's eye; and
capturing reflections of the second signal off of the optical components of the patient's eye.

14. The method of claim 13, wherein each set of refractive indices of the plurality of sets of refractive indices comprises a refractive index for at least one of the optical components of the patient's eye.

15. The method of claim 11, wherein a difference between the first angle relative to the line of sight of the patient's eye and the second angle relative to the line of sight of the patient's eye is obtained based on moving an imaging device relative to the patient's eye.

* * * * *